United States Patent
Goldenberg et al.

(10) Patent No.: US 7,641,901 B2
(45) Date of Patent: *Jan. 5, 2010

(54) IMMUNOTHERAPY OF AUTOIMMUNE DISORDERS USING ANTIBODIES WHICH TARGET B-CELLS

(75) Inventors: David M. Goldenberg, Mendham, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 404 days.

This patent is subject to a terminal disclaimer.

(21) Appl. No.: 11/222,838

(22) Filed: Sep. 12, 2005

(65) Prior Publication Data

US 2006/0051349 A1    Mar. 9, 2006

Related U.S. Application Data

(62) Division of application No. 09/590,284, filed on Jun. 9, 2000, now Pat. No. 7,074,403.

(60) Provisional application No. 60/138,284, filed on Jun. 9, 1999.

(51) Int. Cl.
*A61K 39/395* (2006.01)
*A61K 38/21* (2006.01)
*C12P 21/08* (2006.01)

(52) U.S. Cl. .............. 424/130.1; 424/133.1; 424/134.1; 424/136.1; 424/141.1; 424/144.1; 424/152.1; 424/155.1; 424/172.1; 424/174.1; 424/85.1; 424/85.4; 530/387.1; 530/387.3; 530/388.1; 530/388.2; 530/388.22; 530/388.7; 530/388.73; 530/389.1; 530/389.6; 514/885; 514/903

(58) Field of Classification Search .............. 424/130.1, 424/133.1, 143.1, 153.1, 173.1, 134.1, 136.1, 424/141.1, 144.1, 152.1, 155.1, 172.1, 174.1, 424/85.1, 85.4; 530/387.1, 388.1, 388.2, 530/388.22, 388.7, 388.73, 389.1, 389.6; 514/885, 903

See application file for complete search history.

(56) References Cited

U.S. PATENT DOCUMENTS

| | | | |
|---|---|---|---|
| 5,484,892 A | | 1/1996 | Tedder et al. |
| 5,593,676 A | | 1/1997 | Bhat |
| 5,679,640 A | * | 10/1997 | Gaeta et al. .................... 514/14 |
| 5,686,072 A | | 11/1997 | Uhr et al. |
| 5,750,105 A | * | 5/1998 | Newman et al. ......... 424/133.1 |
| 5,776,093 A | | 7/1998 | Goldenberg |
| 5,776,456 A | | 7/1998 | Anderson et al. |
| 5,795,967 A | | 8/1998 | Aggarwal et al. |
| 6,051,228 A | | 4/2000 | Aruffo et al. |
| 6,090,365 A | | 7/2000 | Kaminski |
| 6,306,393 B1 | | 10/2001 | Goldenberg |
| 6,846,476 B2 | | 1/2005 | White |

FOREIGN PATENT DOCUMENTS

| | | |
|---|---|---|
| EP | 0 332 865 A2 | 2/1989 |
| WO | WO 91/13974 | 9/1991 |
| WO | WO 93/19668 A1 | 10/1993 |
| WO | WO 94/27638 | 12/1994 |
| WO | WO 99/54440 | 10/1999 |
| WO | WO0067796 A1 | 11/2000 |

OTHER PUBLICATIONS

Inaoki, M. et al., J. Exp. Med., 186(11): 1923-1931, 1997.*
Maloney, D.G. et al., Blood, 90(6): 2188-2195, 1997.*
Aozasa, K. et al., Mod. Pathol., 6(2): 121-124, 1993; abstract only.*
Brozek, C.M, et al. J. Clin. Lab. Immunol., 31(3): 105-109, 1990; abstract only.*
Li, J.-L., et al. Cellular Immunology, 118: 85-99, 1989.*
Hildebrandt, S. et al. Annals of the Rheumatic Diseases, 47: 588-594, 1988.*
Leung et al., Mol. Immunol. 1995; 32(17/18); 1413-1427.
The Merck Manual of Diagnosis and Therapy (Seventeenth Edition, Beers et al. eds., Merck Research Laboratories, Whitehouse Station, NJ, 1999; Chapter 180 "Demyelinating Diseases", pp. 1474-1476.
Pawlak-Byczkowska et al., Two New Monoclonal Antibodies, EPB-1 and EPB-2, Reactive with Human Lymphoma; Cancer Research; 49, No. 16, 4568-4577, 1989.
Shih et al., Internalization and Intracellular Processing of an Anti-B-Cell Lymphoma Monoclonal Antibody, LL2; Int.J.Cancer: 56, 538-545, 1994.
Leung et al., Chimerization of LL2, a Rapidly Internalizing Antibody Specific For B Cell Lymphoma; Hybridoma: 13, No. 6, 469-476, 1994.
Ghetie et al., Evaluation of Ricin A Chain-Containing Immunotoxins Directed Against CD19 and CD22 Antigens on Normal and Malignant Human B-Cells as Potential Reagents for in Vico Therapy; Cancer Research: 48, No. 9, 2313-2634, 1988.

(Continued)

*Primary Examiner*—Anne L Holleran
(74) *Attorney, Agent, or Firm*—Rossi, Kimms & McDowell LLP

(57) ABSTRACT

Antibodies that bind with a B-cell antigen provide an effective means to treat autoimmune disorders. Antibodies and fragments, which may be conjugated or naked, are used alone or in multimodal therapies. The antibodies may be bispecific antibodies which may be produced recombinantly as fusion proteins, or as hybrid, polyspecific antibodies.

47 Claims, No Drawings

OTHER PUBLICATIONS

Hekman et al., Initial Experience with Treatment of Human B Cell Lymphoma With Anti-CD19 Monoclonal Antibody; Cancer Immunology Immunotherapy: 32, 364-372, 1991.

Kaminski et al., Radioimmunotheraphy of B-Cell Lymphoma with [131I] Anti-B1 (Anti-CD20) Antibody; The New England Journal of Medicine: 329, No. 7, 459-465, 1993.

Press et al., Radiolabeled-Antibody Therapy of B-Cell Lymphoma with Autologous Bone Marrow Support; The New England Journal of Medicine: 329, No. 17, 1219-1224, 1993.

Maloney et al., Phase I Clinical Trial Using Escalating Single-Dose Infusion Of Chimeric Anti-CD20 Monoclonal Antibody (IDEC-C2B8) in Patients with Recurrent B-Cell Lymphoma; Journal of the American Society of Hematology: 84, No. 8, 2457-2466, 1994.

Press et al., Phase II Trial of $^{131}$I-B1 (anti-CD20) antibody Therapy with Autologous Stem Cell Transplantation for Relapsed B Cell Lymphomas; The Lancet: 346, No. 8971, 336-340, 1995.

Longo, Immunotherapy for Non-Hodgkin's Lymphoma: Current Opinion in Oncology: 8, No. 5, 353-359, 1996.

Hess et al., "Specificity of Effector T Lymphocytes in Autologous Graft-Versus-Host Disease: Role of the Major Histocompatibility Complex Class II Invariant Chain Peptide", Blood, Mar. 1997, pp. 2203-2209, vol. 89, No. 6.

Todd D. Levine et al., "IgM antibody-related polyneuropathies: B-cell depletion chemotherapy using Rituximab.", Neurology, vol. 52, No. 8, pp. 1701-1704, May 12, 1999, XP-000942610.

A. Protheroe et al., "Remission of inflammatory arthropathy in association with anti-CD20 therapy for non-Hodgkin's lymphoma.", Rheumatology, vol. 38, No. 11, pp. 1150-1152, Nov. 1999, XP-000942661.

Zhengxing Qu et al,, "Carbohydrates engineered at antibody constant domains can be used for site-specific conjugation of drugs and chelates", Journal of Immunological Methods, vol. 213, No. 2, pp. 131-144, Apr. 15, 1998, XP-0002103672.

W. Rowan et al., "Cross-linking of the Campath-1 antigen (CD52) mediates growth inhibition in human B-and T-lymphoma cell lines, and subsequent *emergence* of CD52-deficient *cells*.", Immunology, vol. 95, No. 3, pp. 427-436, Nov. 1998, XP-000942636.

Rhona Stein et al., "Epitope specificity of the anti-(B cell lymphoma) monoclonal antibody, LL2.", Cancer Immunology Immunotherapy, vol. 37, No. 5, pp. 293-298,1993, XP-002070322.

Stamatios Theocharis et al., "Characterization of in Vivo Mutated T Cell Clones form Patients Lupus Erythematosus.", Clinical Immunology and Immunopathology, vol. 74, No. 2, pp. 135-142, Feb. 1995, XP-000942609.

\* cited by examiner ic-C2B8," has activity against B-cell lymphomas when provided as unconjugated antibodies at repeated injections of doses exceeding 500 mg per injection. Maloney et al., *Blood* 84:2457 (1994); Longo, *Curr. Opin. Oncol.* 8:353 (1996). About 50 percent of non-Hodgkin's patients, having the low-grade indolent form, treated with this regimen showed responses. Therapeutic responses have also been obtained using $^{131}$I-labeled B1 anti-CD-20 murine monoclonal antibody when provided as repeated doses exceeding 600 mg per injection. Kaminski et al., *N. Engl. J. Med.* 329:459 (1993); Press et al., *N. Engl. J. Med.* 329:1219 (1993); Press et al., *Lancet* 346:336 (1995). However, these antibodies, whether provided as unconjugated forms or radiolabeled forms, have shown only modest activity in patients with the more prevalent and lethal form of B-cell lymphoma, the intermediate or aggressive type.

IMMUNOTHERAPY OF AUTOIMMUNE DISORDERS USING ANTIBODIES WHICH TARGET B-CELLS

This application is a divisional application of U.S. patent application Ser. No. 09/590,284 filed Jun. 9, 2000, now U.S. Pat. No. 7,074,403; which claims priority to U.S. Provisional Application No. 60/138,284 filed Jun. 9, 1999, the contents of which is incorporated by reference in its entirety.

BACKGROUND OF THE INVENTION

1. Field of the Invention

The present invention relates to immunotherapeutic methods for treating autoimmune disorders. In particular, this invention is directed to methods for treating autoimmune disorders by administering antibodies that bind to a B-cell antigen, such as the CD22, CD20, CD19, and CD74 or HLA-DR antigen. The antibodies are administered alone or in combination, and may be naked or conjugated to a drug, toxin or therapeutic radioisotope. Bispecific antibody fusion proteins which bind to the B-cell antigens can be used according to the present invention, including hybrid antibodies which bind to more than one B-cell antigen. The present invention also is directed to multimodal therapeutic methods in which the antibody administration is supplemented by administration of other therapeutic modalities.

2. Background

Antibodies against the CD20 antigen have been investigated for the therapy of B-cell lymphomas. For example, a chimeric anti-CD20 antibody, designated as "IDEC-C2B8," has activity against B-cell lymphomas when provided as unconjugated antibodies at repeated injections of doses exceeding 500 mg per injection. Maloney et al., *Blood* 84:2457 (1994); Longo, *Curr. Opin. Oncol.* 8:353 (1996). About 50 percent of non-Hodgkin's patients, having the low-grade indolent form, treated with this regimen showed responses. Therapeutic responses have also been obtained using $^{131}$I-labeled B1 anti-CD-20 murine monoclonal antibody when provided as repeated doses exceeding 600 mg per injection. Kaminski et al., *N. Engl. J. Med.* 329:459 (1993); Press et al., *N. Engl. J. Med.* 329:1219 (1993); Press et al., *Lancet* 346:336 (1995). However, these antibodies, whether provided as unconjugated forms or radiolabeled forms, have shown only modest activity in patients with the more prevalent and lethal form of B-cell lymphoma, the intermediate or aggressive type.

Autoimmune diseases are a class of diseases associated with a B-cell disorder. Examples include immune-mediated thrombocytopenias, such as acute idiopathic thrombocytopenic purpura and chronic idiopathic thrombocytopenic purpura, myasthenia gravis, lupus nephritis, lupus erythematosus, and rheumatoid arthritis. The most common treatments are corticosteroids and cytotoxic drugs, which can be very toxic. These drugs also suppress the entire immune system, can result in serious infection, and have adverse affects on the liver and kidneys. Other therapeutics that have been used to treat Class III autoimmune diseases to date have been directed against T-cells and macrophages. A need remains for more effective methods of treating autoimmune diseases, particularly Class III autoimmune diseases.

SUMMARY OF THE INVENTION

Accordingly, it is an object of the present invention to provide a method for treating autoimmune diseases using antibody to a B-cell antigen.

It is another object of the invention is to use comparatively low doses of a naked antibody to a B-cell antigen, preferably to CD22 antigen, or a combination of naked antibodies to a CD22 antigen and another B-cell antigen, preferably CD20 and/or CD74.

Yet another object of the invention is to use a combination of one or more naked antibodies to B-cell antigens and/or antibodies to B-cell antigens which are conjugated to drugs, toxins or therapeutic radioisotopes.

It is a further object of this invention to provide multimodal methods for treatment of autoimmune diseases in which a naked or conjugated antibody to a B-cell antigen is supplemented with the administration of other therapeutic modalities, such as those directed against T-cells, plasma cells and macrophages.

These and other objects are achieved, in accordance with one embodiment of the present invention, by the provision of a method of treating an autoimmune disease, comprising the step of administering to a subject having an autoimmune disease an antibody to a B-cell antigen and a pharmaceutically acceptable carrier.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

1. Overview

B-cell clones that bear autoantibody Ig-receptors are present in normal individuals. Autoimmunity results when these B-cells become overactive, and mature to plasma cells that secrete autoantibody. In accordance with the present invention, autoimmune disorders can be treated by administering an antibody that binds to a B-cell antigen, such as the CD22, CD20, CD19, and CD74 or HLA-DR antigen. In one embodiment, comparatively low doses of an entire, naked antibody or combination of entire, naked antibodies are used. In other embodiments, conjugates of such antibodies with drugs, toxins or therapeutic radioisotopes are useful. Bispecific antibody fusion proteins which bind to the B-cell antigens can be used according to the present invention, including hybrid antibodies which bind to more than one B-cell antigen. Preferably the bispecific and hybrid antibodies additionally target a T-cell, plasma cell or macrophage antigen. The present invention also is directed to multimodal therapeutic methods in which the antibody administration is supplemented by administration of other therapeutic modalities.

2. Definitions

In the description that follows, and in documents incorporated by reference, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent when the promoter is a constitutive promoter.

An isolated DNA molecule is a fragment of DNA that is not integrated in the genomic DNA of an organism. For example, a cloned antibody gene is a DNA fragment that has been separated from the genomic DNA of a mammalian cell. Another example of an isolated DNA molecule is a chemically synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from a mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

As used herein, antibody encompasses naked antibodies and conjugated antibodies and antibody fragments, which may be monospecific or multispecific. It includes both polyclonal and monoclonal antibodies, as well as certain recombinant antibodies, such as chimeric and humanized antibodies and fusion proteins.

A chimeric antibody is a recombinant protein that contains the variable domains and complementary determining regions derived from a rodent antibody, while the remainder of the antibody molecule is derived from a human antibody.

Humanized antibodies are recombinant proteins in which murine complementarity determining regions of a monoclonal antibody have been transferred from heavy and light variable chains of the murine immunoglobulin into a human variable domain.

Human antibodies are antibodies that either are isolated from humans and then grown out in culture or are made using animals whose immune systems have been altered so that they respond to antigen stimulation by producing human antibodies.

As used herein, a therapeutic agent is a molecule or atom, which is conjugated to an antibody moiety to produce a conjugate which is useful for therapy. Examples of therapeutic agents include drugs, toxins, enzymes, hormones, cytokines, immunomodulators, boron compounds and therapeutic radioisotopes. Preferred therapeutic radioisotopes include beta, alpha, and Auger emitters, with a kev range of 80-500 kev. Exemplary therapeutic radioisotopes include $^{198}$Au, $^{32}$P, $^{125}$I, $^{131}$I, $^{90}$Y, $^{186}$Re, $^{188}$Re, $^{67}$Cu, and $^{211}$At.

A naked antibody is an entire antibody which is not conjugated with a therapeutic agent. Naked antibodies include both polyclonal and monoclonal antibodies, as well as certain recombinant antibodies, such as chimeric and humanized antibodies.

A conjugated antibody is an antibody or antibody fragment that is conjugated to a therapeutic agent.

A multispecific antibody is an antibody which can bind simultaneously to at least two targets which are of different structure, e.g., two different antigens, two different epitopes on the same antigen, or a hapten and/or an antigen or epitope. One specificity would be for a B-cell antigen or epitope.

A bispecific antibody is an antibody which can bind simultaneously to two targets which are of different structure. Bispecific antibodies (bsAb) and bispecific antibody fragments (bsFab) have at least one arm that specifically binds to a B-cell antigen or epitope and at least one other arm that specifically binds a targetable conjugate.

A fusion protein is a recombinantly produced antigen-binding molecule in which two or more different single-chain antibody or antibody fragment segments with the same or different specificities are linked. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

3. Production of Monoclonal Antibodies, Humanized Antibodies, Primate Antibodies and Human Antibodies Anti-CD20, anti-CD22, anti-CD19, and anti-CD74 antibodies are known generally to those of skill in the art. See, for example, Ghetie et al., *Cancer Res.* 48:2610 (1988); Hekman et al., *Cancer Immunol. Immunother.* 32:364 (1991); Kaminski et al., *N. Engl. J. Med.* 329:459 (1993); Press et al., *N. Engl. J. Med.* 329:1219 (1993); Maloney et al., *Blood* 84:2457 (1994); Press et al., *Lancet* 346:336 (1995); Longo, *Curr. Opin. Oncol.* 8:353 (1996). More particularly, rodent monoclonal antibodies to CD22, CD20, CD19, or CD74 antigens can be obtained by methods known to those skilled in the art. See generally, for example, Kohler and Milstein, *Nature* 256:495 (1975), and Coligan et al. (eds.), CURRENT PROTOCOLS IN IMMUNOLOGY, VOL. 1, pages 2.5.1-2.6.7 (John Wiley & Sons 1991) ["Coligan"]. Briefly, monoclonal antibodies can be obtained by injecting mice with a composition comprising the antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen that was injected, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Suitable amounts of well-characterized antigen for production of antibodies can be obtained using standard techniques. As an example, CD22 can be immunoprecipitated from B-lymphocyte protein using the deposited antibodies described by Tedder et al., U.S. Pat. No. 5,484,892 (1996).

Alternatively, CD22, CD20, CD19, or CD74 antigen proteins can be obtained from transfected cultured cells that overproduce the antigen of interest. Expression vectors that comprise DNA molecules encoding each of these proteins can be constructed using published nucleotide sequences. See, for example, Wilson et al., *J. Exp. Med.* 173:137 (1991); Wilson et al., *J. Immunol.* 150:5013 (1993). As an illustration, DNA molecules encoding CD22 can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., *Gene* 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize genes as large as 1.8 kilobases in length. Adang et al., *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993).

In a variation of this approach, monoclonal antibody can be obtained by fusing myeloma cells with spleen cells from mice immunized with a murine pre-B cell line stably transfected with cDNA which encodes the antigen of interest. See Tedder et al., U.S. Pat. No. 5,484,892 (1996).

One example of a suitable murine anti-CD22 monoclonal antibody is the LL2, deposited on May 27, 2005 with the American Type Culture Collection, 10801 University Boulevard, Manassas, Va. 20110-2209 (ATCC Accession No. PTA-6735), (formerly EPB-2) monoclonal antibody, which was produced against human Raji cells derived from a Burkitt lymphoma. Pawlak-Byczkowska et al., *Cancer Res.* 49:4568 (1989). This monoclonal antibody has an $IgG_{2a}$ isotype, and the antibody is rapidly internalized into lymphoma cells. Shih et al, *Int. J. Cancer* 56:538 (1994). Immunostaining and in vivo radioimmunodetection studies have demonstrated the excellent sensitivity of LL2 in detecting B-cell lymphomas. Pawlak-Byczkowska et al., *Cancer Res.* 49:4568 (1989); Murthy et al., *Eur. J. Nuc. Med* 19:394 (1992). Moreover, $^{99m}$Tc-labeled LL2-Fab' fragments have been shown to be useful in following upstaging of B-cell lymphomas, while $^{131}$I-labeled intact LL2 and labeled LL2 F(ab')$_2$ fragments have been used to target lymphoma sites and to induce therapeutic responses. Murthy et al., *Eur. J. Nuc. Med.* 19:394 (1992); Mills et al., *Proc. Am. Assoc. Cancer Res.* 34:479 (1993) [Abstract 2857]; Baum et al., *Cancer* 73 (*Suppl.* 3):896 (1994); Goldenberg et al., *J. Clin. Oncol.* 9:548 (1991). Furthermore, Fab' LL2 fragments conjugated with a derivative of Pseudomonas exotoxin has been shown to induce complete remissions for measurable human lymphoma xenografts growing in nude mice. Kreitman et al., *Cancer Res.* 53:819 (1993). An example of an anti-CD74 antibody is the LL1 antibody.

In an additional embodiment, an antibody of the present invention is a chimeric antibody in which the variable regions of a human antibody have been replaced by the variable regions of a rodent anti-CD22 antibody. The advantages of chimeric antibodies include decreased immunogenicity and increased in vivo stability.

Techniques for constructing chimeric antibodies are well known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody with respective human κ and $IgG_1$ constant region domains. This publication also provides the nucleotide sequences of the LL2 light and heavy chain variable regions, $V_\kappa$ and $V_H$, respectively.

In another embodiment, an antibody of the present invention is a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46: 310 (1990).

In yet another embodiment, an antibody of the present invention is a "humanized" monoclonal antibody. That is, mouse complementarity determining regions are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., *Proc. Nat'l Acad. Sci. USA* 86: 3833 (1989). Techniques for producing humanized monoclonal antibodies are described, for example, by Jones et al., *Nature* 321:522 (1986), Riechmann et al., *Nature* 332:323 (1988), Verhoeyen et al., *Science* 239: 1534 (1988), Carter et al., *Proc. Nat'l Acad. Sci. USA* 89:4285 (1992), Sandhu, *Crit. Rev. Biotech.* 12:437 (1992), and Singer et al., *J. Immun.* 150:2844 (1993). The publication of Leung et al., *Mol. Immunol.* 32:1413 (1995), describes the construction of humanized LL2 antibody.

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994).

4. Production of Bispecific Antibodies

The present invention also may employ a bispecific antibody (bsAb) or antibody fragment (bsFab) having at least one arm that specifically binds to a B-cell antigen and at least one other arm that specifically binds a targetable conjugate. The targetable conjugate comprises a carrier portion which comprises or bears at least one epitope recognized by at least one arm of the bispecific antibody or antibody fragment. In a preferred embodiment, the epitope is a hapten. In an alternative embodiment, the epitope is a part of the carrier. Examples of recognizable haptens include, but are not limited to, chelators, such as DTPA, fluorescein isothiocyanate, vitamin B-12 and other moieties to which specific antibodies can be raised. The carrier portion also may be conjugated to a variety of agents. Examples of conjugated agents include, but are not limited to, metal chelate complexes, drugs, toxins and other effector molecules, such as cytokines, lymphokines, chemokines, immunomodulators, radiosensitizers, asparaginase, carboranes and radioactive halogens. Additionally, enzymes useful for activating a prodrug or increasing the target-specific toxicity of a drug can be conjugated to the carrier. Thus, the use of bispecific antibodies and fragments which have at least one arm that specifically binds a targetable conjugate allows a variety of therapeutic and diagnostic applications to be performed without raising new bsAb for each application.

The present invention encompasses antibodies and antibody fragments. The antibody fragments are antigen binding portions of an antibody, such as F(ab')2, F(ab)2, Fab', Fab, and the like. The antibody fragments bind to the same antigen that is recognized by the intact antibody. For example, an anti-CD22 monoclonal antibody fragment binds to an epitope of CD22. The bsAb of the present invention include, but are not limited to, IgG×IgG, IgG×F(ab')2, IgG×Fab', IgG×scFv, F(ab')2×F(ab')2, Fab'×F(ab')2, Fab'×Fab', Fab'×scFv and scFv×scFv bsmabs. Also, species such as scFv×IgG×scFv and Fab'×IgG×Fab', scFv×F(ab')2×scFv and Fab'×F(ab')2× Fab' are included.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the hypervariable region.

5. Production of Fusion Proteins

Another method for producing bsAbs is to engineer recombinant fusion proteins linking two or more different single-chain antibody or antibody fragment segments with the needed dual specificities. See, e.g., Coloma et al., *Nature Biotech.* 15:159-163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Functional bispecific single-chain antibodies (bscAb), also called diabodies, can be produced in mammalian cells using recombinant methods. See, e.g., Mack et al., *Proc. Natl. Acad. Sci.*, 92: 7021-7025, 1995. For example, bscAb are produced by joining two single-chain Fv fragments via a glycine-serine linker using recombinant methods. The V light-chain (VL) and V heavy-chain (VH) domains of two antibodies of interest are isolated using standard PCR methods. The VL and VH cDNA's obtained from each hybridoma are then joined to form a single-chain fragment in a two-step fusion PCR. The first PCR step introduces the (Gly4-Ser1)3 linker, and the second step joins the VL and VH amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Recombinant methods can be used to produce a variety of fusion proteins.

6. Coupling of Antibodies to Lipid Emulsions

Long-circulating sub-micron lipid emulsions, stabilized with poly(ethylene glycol)-modified phosphatidylethanolamine (PEG-PE), can be used as drug carriers for the antibodies of the present invention. The emulsions are composed of two major parts: an oil core, e.g., triglyceride, stabilized by emulsifiers, e.g., phospholipids. The poor emulsifying properties of phospholipids can be enhanced by adding a biocompatible co-emulsifier such as polysorbate 80. In a preferred embodiment, the antibody is conjugated to the surface of the lipid emulsion globules with a poly(ethylene glycol)-based, heterobifunctional coupling agent, poly(ethylene glycol)-vinylsulfone-N-hydroxy-succinimidyl ester (NHS-PEG-VS).

The submicron lipid emulsion is prepared and characterized as described. Lundberg, *J. Pharm. Sci.*, 83:72 (1993); Lundberg et al., *Int. J. Pharm.*, 134:119 (1996). The basic composition of the lipid emulsion is triolein:DPPC:polysorbate 80, 2:1:0.4 (w/w). When indicated, PEG-DPPE is added into the lipid mixture at an amount of 2-8 mol % calculated on DPPC.

The coupling procedure starts with the reaction of the NHS ester group of NHS-PEG-VS with the amino group of distearoyl phosphatidyl-ethanolamine (DSPE). Twenty-five µmol of NHS-PEG-VS are reacted with 23 µmol of DSPE and 50 µmol triethylamine in 1 ml of chloroform for 6 hours at 40° C. to produce a poly(ethylene glycol) derivative of phosphatidyl-ethanolamine with a vinylsulfone group at the distal terminus of the poly(ethylene glycol) chain (DSPE-PEG-VS). For antibody conjugation, DSPE-PEG-VS is included in the lipid emulsion at 2 mol % of DPPC. The components are dispersed into vials from stock solutions at −20° C., the solvent is evaporated to dryness under reduced pressure. Phosphate-buffered saline (PBS) is added, the mixture is heated to 50° C., vortexed for 30 seconds and sonicated with a MSE probe sonicator for 1 minute. Emulsions can be stored at 4° C., and preferably are used for conjugation within 24 hours.

Coupling of antibodies to emulsion globules is performed via a reaction between the vinylsulfone group at the distal PEG terminus on the surface of the globules and free thiol groups on the antibody. Vinylsulfone is an attractive derivative for selective coupling to thiol groups. At approximately neutral pH, VS will couple with a half life of 15-20 minutes to proteins containing thiol groups. The reactivity of VS is slightly less than that of maleimide, but the VS group is more stable in water and a stable linkage is produced from reaction with thiol groups.

Before conjugation, the antibody is reduced by 50 mM 2-mercaptoethanol for 10 minutes at 4° C. in 0.2 M Tris buffer (pH 8.7). The reduced antibody is separated from excess 2-mercaptoethanol with a Sephadex G-25 spin column, equilibrated in 50 mM sodium acetate buffered 0.9% saline (pH 5.3). The product is assayed for protein concentration by measuring its absorbance at 280 nm (and assuming that a 1 mg/ml antibody solution of 1.4) or by quantitation of $^{125}$I- labeled antibody. Thiol groups are determined with Aldrithiol[9] following the change in absorbance at 343 nm and with cystein as standard.

The coupling reaction is performed in HEPES-buffered saline (pH 7.4) overnight at ambient temperature under argon. Excess vinylsulfone groups are quenched with 2 mM 2-mercaptoethanol for 30 minutes, excess 2-mercaptoethanol and antibody are removed by gel chromatography on a Sepharose CL-48 column. The immunoconjugates are collected near the void volume of the column, sterilized by passage through a 0.45 μm sterile filter, and stored at 4° C.

Coupling efficiency is calculated using $^{125}$I-labeled antibody. Recovery of emulsions is estimated from measurements of [$^{14}$C]DPPC in parallel experiments. The conjugation of reduced LL2 to the VS group of surface-grafted DSPE-PEG-VS is very reproducible with a typical efficiency of near 85%.

7. Therapeutic Use of Antibodies in Simple and Multimodal Regimens

The present invention contemplates the use of naked and/or conjugated antibodies as the primary therapeutic composition for treatment of autoimmune diseases. Such a composition can contain polyclonal antibodies or monoclonal antibodies. Preferred antibodies are anti-CD22 antibodies, such as LL2 antibodies, including murine LL2 monoclonal antibody, chimeric LL2 antibody, and humanized LL2 antibody. Antibodies to a single B-cell antigen or to more than one B-cell antigen may be used. In a preferred embodiment, bispecific antibodies and fusion proteins which comprise specificities for more than one B-cell antigen or epitope are employed.

For example, a therapeutic composition of the present invention can contain a mixture of monoclonal naked anti-CD22 antibodies directed to different, non-blocking CD22 epitopes. Monoclonal antibody cross-inhibition studies have identified five epitopes on CD22, designated as epitopes A-E. See, for example, Schwartz-Albiez et al., "The Carbohydrate Moiety of the CD22 Antigen Can Be Modulated by Inhibitors of the Glycosylation Pathway," in LEUKOCYTE TYPING IV. WHITE CELL DIFFERENTIATION ANTIGENS, Knapp et al. (eds.), p. 65 (Oxford University Press 1989). As an illustration, the LL2 antibody binds with epitope B. Stein et al., Cancer Immunol. Immunother. 37:293 (1993). Accordingly, the present invention contemplates therapeutic compositions comprising a mixture of monoclonal anti-CD22 antibodies that bind at least two CD22 epitopes. For example, such a mixture can contain monoclonal antibodies that bind with at least two CD22 epitopes selected from the group consisting of epitope A, epitope B, epitope C, epitope D and epitope E.

Methods for determining the binding specificity of an anti-CD22 antibody are well-known to those of skill in the art. General methods are provided, for example, by Mole, "Epitope Mapping," in METHODS IN MOLECULAR BIOLOGY, VOLUME 10: IMMUNOCHEMICAL PROTOCOLS, Manson (ed.), pages 105-116 (The Humana Press, Inc. 1992). More specifically, competitive blocking assays to determine CD22 epitope specificity are described by Stein et al., Cancer Immunol. Immunother. 37:293 (1993), and by Tedder et al., U.S. Pat. No. 5,484,892 (1996).

The Tedder patent also describes the production of CD22 mutants, which lack one or more immunoglobulin-like domains. These mutant proteins were used to determine that immunoglobulin-like domains 1, 2, 3, and 4 correspond with epitopes A, D, B, and C, respectively. Thus, binding a test antibody with a panel of CD22 proteins lacking particular immunoglobulin-like domain can also identify CD22 epitope specificity.

The therapeutic compositions described herein are useful for treatment of autoimmune diseases, particularly for the treatment of Class III autoimmune diseases including immune-mediated thrombocytopenias, such as acute idiopathic thrombocytopenic purpura and chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis. In this context, the therapeutic compositions are used to deplete the blood of normal B-cells for an extended period.

Although naked, preferably anti-CD22, antibodies are the preferred, primary therapeutic compositions for treatment of autoimmune diseases, the efficacy of such naked antibody therapy can be enhanced by supplementing the naked antibodies with other therapies described herein. In such multimodal regimens, the supplemental therapeutic compositions can be administered before, concurrently or after administration of the naked, preferably anti-CD22, antibodies. Multimodal therapy of Class III autoimmune diseases may comprise co-administration of therapeutics that are targeted against T-cells, plasma cells or macrophages, such as antibodies directed against T-cell epitopes, more particularly against the CD4 and CD5 epitopes. Gamma globulins also may be co-administered. In some cases, it may be desirable to co-administer immunosuppressive drugs such as corticosteroids and possibly also cytotoxic drugs. In this case, lower doses of the corticosteroids and cytotoxic drugs can be used as compared to the doses used in conventional therapies, thereby reducing the negative side effects of these therapeutics. The supplemental therapeutic compositions can be administered before, concurrently or after administration of the naked B-cell, preferably anti-CD22, antibodies.

In an alternative embodiment, the antibodies to the CD22, CD20, CD19, and CD74 or HLA-DR antigen are conjugated to a drug, toxin, enzyme, hormone, cytokine, immunomodulator, boron compound or therapeutic radioisotope, or a fusion protein of an antibody and a toxin may be used. These conjugates and fusion proteins may be used alone, or in combination with naked B-cell antibodies. In a further preferred embodiment, an antibody is used that comprises an arm that is specific for a low-molecular weight hapten to which a therapeutic agent is conjugated or fused. In this case, the antibody pretargets the B-cells, and the low-molecular weight hapten with the attached therapeutic agent is administered after the antibody has bound to the B-cell targets. Examples of recognizable haptens include, but are not limited to, chelators, such as DTPA, fluorescein isothiocyanate, vitamin B-12 and other moieties to which specific antibodies can be raised.

Drugs which are known to act on B-cells, plasma cells and/or T-cells are particularly useful in accordance with the present invention, whether conjugated to a B-cell antibody, or administered as a separate component in combination with a naked or conjugated B-cell antibody. These include methotrexate, phenyl butyrate, bryostatin, cyclophosphamide, etoposide, bleomycin, doxorubicin, carmustine, vincristine, procarbazine, dexamethasone, leucovorin, prednisone, maytansinoids such as DM1, calicheamicin, rapamycin, leflunomide, FK506, immuran, fludarabine, azathiopine, mycophenolate, and cyclosporin. Drugs such as immuran, methotrexate, and fludarabine which act on both B-cells and T-cells are particularly preferred. Illustrative of toxins which are suitably employed in accordance with the present invention are ricin, abrin, ribonuclease, DNase I, Staphylococcal enterotoxin-A, pokeweed antiviral protein, gelonin, diphtherin toxin, Pseudomonas exotoxin, Pseudomonas endotoxin and RNAses, such as onconase. See, for example, Pastan et al., Cell 47:641 (1986), and Goldenberg, C A—A Cancer Journal for Clinicians 44:43 (1994). Other suitable drugs and toxins are known to those of skill in the art.

Cytokine agonists and antagonists may also be used in multimodal therapies according to the present invention. Tumor necrosis factor alpha (TNFα) and interleukin-1 (IL-1) are important in mediating inflammation in rheumatoid arthritis. Accordingly, anti-TNFα reagents, such as Infximab and Etanercept (Embrel), are useful in multimodal therapy according to the invention, as well as anti-IL-1 reagents.

Other useful secondary therapeutics useful in multimodal therapies are IL-2 and GM-CSF, which may be conjugated with an anti-B-cell antibody, or combined with a naked anti-B-cell antibody as a separate component.

In general, the dosage of administered antibodies will vary depending upon such factors as the patient's age, weight, height, sex, general medical condition and previous medical history. Typically, it is desirable to provide the recipient with a dosage of antibody component, immunoconjugate or fusion protein which is in the range of from about 1 pg/kg to 10 mg/kg (amount of agent/body weight of patient), although a lower or higher dosage also may be administered as circumstances dictate.

Administration of antibodies to a patient can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Intravenous injection provides a useful mode of administration due to the thoroughness of the circulation in rapidly distributing antibodies.

In preferred embodiments, naked anti-B-cell antibodies, particularly anti-CD22 antibodies, are administered at low protein doses, such as 20 milligrams to 2 grams protein per dose, given once, or repeatedly, parenterally. Alternatively, naked antibodies are administered in doses of 20 to 1000 milligrams protein per dose, or 20 to 500 milligrams protein per dose, or 20 to 100 milligrams protein per dose.

The antibodies, alone or conjugated to liposomes, can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (1995).

For purposes of therapy, antibodies are administered to a patient in a therapeutically effective amount in a pharmaceutically acceptable carrier. In this regard, a "therapeutically effective amount" is one that is physiologically significant. An agent is physiologically significant if its presence results in a detectable change in the physiology of a recipient patient. In the present context, an agent is physiologically significant if its presence results in the inactivation or killing of targeted B-cells.

Additional pharmaceutical methods may be employed to control the duration of action of an antibody in a therapeutic application. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446 (1992). The rate of release of an antibody from such a matrix depends upon the molecular weight of the protein, the amount of antibody within the matrix, and the size of dispersed particles. Saltzman et al., *Biophys. J.* 55:163 (1989); Sherwood et al., supra. Other solid dosage forms are described in REMINGTON'S PHARMACEUTICAL SCIENCES, 19th ed. (1995).

The present invention, thus generally described, will be understood more readily by reference to the following examples, which are provided by way of illustration and are not intended to be limiting of the present invention.

EXAMPLE 1

Treatment of a Patient with Humanized LL2

A patient undergoes therapy with humanized LL2 monoclonal antibody. The patient was infused intravenously with 634 mg of humanized LL2 antibody, and the treatment was repeated 6, 13, and 20 days following this initial treatment. Immediately following the last dose, the serum value of hLL2 was 389.7 μg/ml, and one month following the last dose the serum value of hLL2 was 186.5 μg/ml. Normal B-cells in the blood prior to therapy with hLL2 were significantly depleted from the blood 2 months post-therapy, and there was minimal reappearance of normal B cells five months post-therapy. The results are shown in the following table.

TABLE 1

B-cells and T-cells in blood

| Day | T4/T8 | % blood B-cells | | | | % blood T-cells | % blood HLA-Dr |
| | | CD19 | CD20 | Kappa | lambda | CD3 | (Ia) |
| | | | | Flow cytometry | | | |
|---|---|---|---|---|---|---|---|
| 0 | 1.5 | 5 | 5 | 6 | 2 | 38 | 6 |
| 28 | | | | hLL2 therapy | | | |
| 34 | | | | hLL2 therapy | | | |
| 41 | | | | hLL2 therapy | | | |
| 48 | | | | hLL2 therapy | | | |
| 76 | 1.3 | <2 | <2 | <1 | <1 | 71 | 6 |
| 191 | 2.0 | <2 | <2 | <1 | <1 | 73 | 4 |

EXAMPLE 2

Treatment of a Patient with Chronic Idiopathic *Thrombocytopenia purpura*

A 50-year-old female with chronic idiopathic thrombocytopenia purpura has been treated with prednisone, gamma globulins, and high dose dexamethason, but the disease progresses. She undergoes splenectomy, which fails to stabilize the disease. Her platelet count falls to less than 20,000/microliter, and hemorraghic events increase in frequency. The patient is then treated with hLL2, 480 mg intravenously each week, for a period of six weeks. Four weeks after the last dose of hLL2, platelet number is increased by 100%, and the hemorraghic events become infrequent. Three months after the last antibody infusion the disease is in remission.

EXAMPLE 3

Treatment of a Patient with Progressive Rheumatoid Arthritis

A 60-year-old male, with severe progressive rheumatoid arthritis of the finger joints, wrists, and elbows, has failed therapy with methotrexate, and obtains only minor relief when placed on Enbrel therapy. The patient is then treated with hLL2, 600 mg intravenously each week, for a period of eight weeks. After 3 weeks a 30% improvement in measures of disease activity is observed, which is maintained for 6 months. The patient is again treated with hLL2, at the same dose and frequency. The patient continues to improve, and 6 months after the second hLL2 therapy, a 70% improvement is observed. No human anti-hLL2 antibodies are observed at any time during, or after the hLL2 therapy. Although normal B-cells are significantly reduced from the blood, no infectious complications, or other drug-related toxicity are observed.

EXAMPLE 4

Treatment of a Patient with Myasthenia Gravis

A 55-year-old male has failed all conventional therapy for myasthenia gravis, and is admitted to a neurological intensive therapy unit. The patient was stabilized by plasma exchange, and given intravenous immunoglobulin to reduce the titer of anti-acetylcholine receptor antibody. The patient remained bedridden, and was then treated with hLL2, 800 mg intravenously each week, for a period of six weeks. One week after the last dose of hLL2, a 70% drop in B-lymphocytes is observed, and a significant drop in the titer of the anti-acetylcholine was observed. Two months after the last hLL2 dose the patient was mobile, and was released from the hospital.

EXAMPLE 5

Combination Therapy of Progressive Rheumatoid Arthritis

Another patient with severe progressive rheumatoid arthritis of the finger joints, wrists, and elbows, has failed therapy with methotrexate, and obtains only minor relief when placed on Enbrel therapy. The patient is then treated with 300 mg each of hLL2 and Rituximab, intravenously each week, for a period of five weeks. Significant improvement in measures of disease activity is observed, which is maintained for 6 months. The patient is again treated with the same regimen and continues to improve. Six months after the second course of therapy, additional improvement is observed. No human anti-hLL2 or anti-Rituximab antibodies are observed at any time during, or after the therapy. Although normal B-cells are significantly reduced from the blood, no infectious complications, or other drug-related toxicity are observed.

EXAMPLE 6

Combination Therapy of Chronic Idiopathic *Thrombocytopenia purpura*

A patient with chronic idiopathic thrombocytopenia purpura has been treated with prednisone, gamma globulins, and high dose dexamethason, but the disease progresses. He undergoes spleenectomy, which fails to stabilize the disease. The platelet count falls to less than 20,000/microliter, and hemorraghic events increase in frequency. This patient is treated with 10 mCi of 90-yttrium-hLL2 and 200 mg of hLL2, followed by 300 mg doses each of hLL2 and Rituximab, intravenously each week, for a period of six weeks. Four weeks after the last dose of hLL2 and Rituximab, platelet number is increased by 150%, and the hemorraghic events become infrequent. Three months after the last antibody infusion the disease is in remission.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for treating an autoimmune disorder comprising administering to a human subject having an autoimmune disorder an effective amount of a therapeutic composition comprising a pharmaceutically acceptable carrier and at least one non-blocking anti-CD22 antibody, wherein said antibody is a naked antibody.

2. The method of claim 1, wherein said therapeutic composition is administered parenterally in a dosage of from 20 to 2000 mg per dose.

3. The method of claim 1, wherein said subject receives said antibody in repeated parenteral dosages.

4. The method of claim 1, wherein said antibody is selected from the group consisting of subhuman primate antibody, murine monoclonal antibody, chimeric antibody, humanized antibody, and human antibody.

5. The method of claim 4, wherein said antibody is a murine, chimeric, human, or humanized LL2 antibody (ATCC Accession No. PTA-6735).

6. The method of claim 1, wherein said autoimmune disease is selected from the group consisting of acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cinhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

7. The method of claim 1, further comprising separately administering a secondary therapeutic directed against T-cells, B-cells, plasma cells, or macrophages or inflammatory cytokines.

8. The method of claim 7, wherein said secondary therapeutic is administered prior to the administration of said therapeutic composition.

9. The method of claim 7, wherein said secondary therapeutic is administered concurrently with the administration of said therapeutic composition.

10. The method of claim 7, wherein said secondary therapeutic is administered after the administration of said therapeutic composition.

11. The method of claim 7, wherein said secondary therapeutic is selected from the group consisting of drugs, toxins, enzymes, hormones, cytokines, immunomodulators, boron compounds and therapeutic radioisotopes.

12. The method according to claim 1, wherein said non-blocking anti-CD22 antibody binds a CD22 epitope selected from the group consisting of epitope A, epitope B, epitope C, epitope D and epitope E.

13. The method according to claim 1, wherein said non-blocking anti-CD22 antibody binds the CD22 epitope recognized by the LL2 antibody (ATCC Accession No. PTA-6735).

14. The method according to claim 1, wherein said autoimmune disease is selected from the group consisting of acute idiopathic thrombocytopenic purpura, chronic idiopathic thrombocytopenic purpura, myasthenia gravis, systemic lupus erythematosus, rheumatoid arthritis, multiple sclerosis, and Sjögren's syndrome.

15. A method according to claim 1, wherein the at least one non-blocking anti-CD22 antibody is in a combination with an antibody selected from the group consisting of an anti-CD19 antibody, an anti-CD20 antibody, an anti-CD74 antibody and an anti-HLA DR antibody.

16. The method of claim 15, wherein said combination comprises an anti-CD 19 antibody.

17. The method of claim 15, wherein said combination comprises an anti-CD20 antibody.

18. The method of claim 15, wherein said combination comprises an anti-CD74 antibody.

19. The method of claim 15, wherein said combination comprises an anti-HLA-DR antibody.

20. The method according to claim 15, wherein said combination comprises a non-blocking anti-CD22 antibody that binds the CD22 epitope recognized by the LL2 antibody (ATOC Accession No. PTA-6735) and an antibody selected from the group consisting of an anti-CD19 antibody, an anti-CD20 antibody, an anti-CD74 antibody and an anti-HLA-DR antibody.

21. The method according to claim 15, wherein said combination comprises an anti-CD22 antibody that binds a CD22 epitope selected from the group consisting of epitope A, epitope B, epitope C, epitope D and epitope E and an antibody selected from the group consisting of an anti-CD 19 antibody, an anti-CD20 antibody, an anti-CD74 antibody and an anti-HLA-DR antibody.

22. The method of claim 1, wherein said naked anti-CD22 antibody binds with epitope B of the CD22 antigen.

23. The method of claim 1, wherein said autoimmune disease is Siogren's syndrome.

24. The method of claim 1, wherein said autoimmune disease is systemic lupus erythematosus.

25. The method of claim 1, wherein said autoimmune disease is rheumatoid arthritis.

26. The method of claim 1, wherein said antibody is a bispecific antibody.

27. A method for treating an autoimmune disorder comprising administering to a human subject having an autoimmune disorder an effective amount of a therapeutic composition comprising a pharmaceutically acceptable carrier and at least one non-blocking anti-CD22 antibody, wherein said therapeutic composition further comprises an anti-CD20 antibody.

28. The method according to claim 27, wherein said non-blocking anti-CD22 antibody is conjugated to a therapeutic agent.

29. The method according to claim 28, wherein said therapeutic agent is a drug, toxin, enzyme, hormone, cytokine, immunomodulator, boron compound or therapeutic radioisotope.

30. The method according to claim 28, wherein said therapeutic agent is conjugated through a chelator.

31. The method of claim 28, wherein said therapeutic agent is a radioisotope.

32. The method of claim 31, wherein said anti-CD20 antibody is a naked antibody.

33. The method of claim 32, wherein said non-blocking anti-CD22 antibody binds with epitope B.

34. The method of claim 32, wherein said non-blocking anti-CD22 antibody binds the CD22 epitope recognized by the LL2 antibody (ATCC Accession No. PTA-6735).

35. The method of claim 34, wherein said autoimmune disease is Siogren's syndrome.

36. The method of claim 34, wherein said autoimmune disease is systemic lupus erythematosus.

37. The method of claim 34, wherein said autoimmune disease is rheumatoid arthritis.

38. A method for treating an autoimmune disorder comprising administering to a human subject having an autoimmune disorder an effective amount of a therapeutic composition comprising a pharmaceutically acceptable carrier and a naked anti-CD20 antibody, a naked non-blocking anti-CD22 antibody that binds with epitope B of the CD22 antigen, and a cytokine.

39. A method for treating an autoimmune disorder comprising administering to a human subject having an autoimmune disorder an effective amount of a therapeutic composition comprising a pharmaceutically acceptable carrier and at least two monoclonal antibodies that bind with distinct CD22 epitopes, wherein the first of said anti-CD22 antibodies is a non-blocking anti-CD22 antibody, that binds with a CD22 epitope selected from the group consisting of epitope A, epitope B, epitope C, epitope D, and epitope E, and wherein the second antibody binds with a different CD22 epitope selected from the group consisting of epitope A, epitope B, epitope C, epitope D and epitope E.

40. A method for treating an autoimmune disorder comprising administering to a human subject having an autoimmune disorder an effective amount of a therapeutic composition comprising a pharmaceutically acceptable carrier and a bispecific antibody fusion protein of a non-blocking anti-CD22 antibody and an antibody selected from the group consisting of an anti-CD 19 antibody, an anti-CD20 antibody, an anti-CD74 antibody and an anti-HLA-DR antibody.

41. The method of claim 40, wherein said bispecific antibody fusion protein is a bispecific antibody fusion protein of a non-blocking anti-CD22 antibody an an anti-CD20 antibody.

42. The method of claim 40, wherein said bispecific antibody fusion protein is a bispecific antibody fusion protein of a non-blocking anti-CD22 antibody an an anti-CD74 antibody.

43. The method of claim 40, wherein said bispecific antibody fusion protein is a bispecific antibody fusion protein of a non-blocking anti-CD22 antibody an an anti-HLA-DR antibody.

44. The method according to claim 40, wherein said bispecific fusion protein is formed from a non-blocking anti-CD22 antibody that binds the CD22 epitope recognized by the LL2 antibody (ATCC Accession No. PTA-6735) and an antibody selected from the group consisting of an anti-CD19 antibody, an anti-CD20 antibody, an anti-CD74 antibody and an anti-HLA-DR antibody.

45. The method according to claim 40 wherein said is a bispecific fusion protein is formed from a non-blocking anti-CD22 antibody that binds CD22 epitope selected from the group consisting of epitope A, epitope B, epitope C, epitope D and epitope E and an antibody selected from the group consisting of an anti-CD 19 antibody, an anti-CD20 antibody, an anti-CD74 antibody and an anti-HLA-DR antibody.

46. The method of claim 40, wherein said bispecific antibody fusion protein is a bispecific antibody fusion protein of a non-blocking anti-CD22 antibody and an anti-CD 19 antibody.

47. A method for treating an autoimmune disorder comprising administering to a human subject having an autoimmune disorder an effective amount of a therapeutic composition comprising a pharmaceutically acceptable carrier and at least one naked anti-CD22 antibody, wherein said anti-CD22 antibody binds with epitope B of the CD22 antigen, and wherein said therapeutic composition is administered concurrently, or sequentially in any order, with a therapeutic composition comprising a pharmaceutically acceptable carrier and a naked anti-CD20 antibody, and a therapeutic composition comprising a pharmaceutically acceptable carrier and a cytokine.

* * * * *

UNITED STATES PATENT AND TRADEMARK OFFICE
CERTIFICATE OF CORRECTION

PATENT NO. : 7,641,901 B2
APPLICATION NO. : 11/222838
DATED : January 5, 2010
INVENTOR(S) : Goldenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this

Sixteenth Day of November, 2010

David J. Kappos
*Director of the United States Patent and Trademark Office*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 1

Gly Gly Gly Gly Ser Gly Gly Gly Gly Ser Gly Gly Gly Gly Ser
 1               5                   10                  15